United States Patent
Nonaka et al.

[11] Patent Number: 5,993,373
[45] Date of Patent: Nov. 30, 1999

[54] ROTATING RADIATION CHAMBER FOR RADIATION THERAPY

[75] Inventors: Hideki Nonaka; Toru Kan, both of Niihama, Japan

[73] Assignee: Sumitomo Heavy Industries, Ltd., Tokyo, Japan

[21] Appl. No.: 09/130,476

[22] Filed: Aug. 7, 1998

[30] Foreign Application Priority Data

Aug. 8, 1997 [JP] Japan .................................. 9-214508

[51] Int. Cl.⁶ .............................. A61N 5/10; A61N 5/00
[52] U.S. Cl. ...................... 600/1; 250/492.1; 250/492.3; 378/64; 378/65; 378/68; 378/69; 378/195
[58] Field of Search .............................. 600/1.2; 604/20; 607/1, 2, 100; 250/492.3, 492.1; 378/65, 68, 69, 64, 195, 194

[56] References Cited

U.S. PATENT DOCUMENTS

| | | | |
|---|---|---|---|
| 3,720,817 | 3/1973 | Dinwiddie | 600/1 |
| 3,757,118 | 9/1973 | Hodge et al. | 250/492.1 |
| 4,172,979 | 10/1979 | Morrison | 378/65 |
| 4,233,519 | 11/1980 | Coad | 378/65 |
| 5,724,400 | 3/1998 | Swerdloff et al. | 378/65 |
| 5,751,781 | 5/1998 | Brown et al. | 378/65 |

FOREIGN PATENT DOCUMENTS

WO89/09906  10/1989  WIPO .

Primary Examiner—Cary O'Connor
Assistant Examiner—Nina Nathan Straub
Attorney, Agent, or Firm—Nikaido, Marmelstein, Murray & Oram LLP

[57] ABSTRACT

A fixed ring rail and a moving ring rail sandwiching a moving route of a radiation beam irradiating section therebetween, forms a cylindrical passage with a semicircular cross-section having a horizontal floor. Upon that passage is placed a moving floor composed of a continuous series of multiple plates which are connected freely flexible with each other. The moving floor is moved in synchrony with the rotation of radiation beam irradiation section, and, at the same time, the moving ring rail is allowed to rotate in the reverse direction by the same distance. A horizontal floor necessary as an access floor to the treatment bed and to the radiation beam irradiating section is formed regardless of the rotating position of the radiation beam irradiation section, and the patient is surrounded completely to remove him/her of fear.

10 Claims, 10 Drawing Sheets

ROTATING RADIATION CHAMBER FOR RADIATION THERAPY

BACKGROUND OF THE INVENTION

1. Field of the Invention

This invention relates to a rotating radiation chamber for radiation therapy which has a radiation beam irradiating section rotatable round a patient, particularly to a rotating radiation chamber for radiation therapy which is suitably used as a rotation gantry of a cancer therapy device by use of a proton beam.

2. Description of the Related Art

Figure 9:
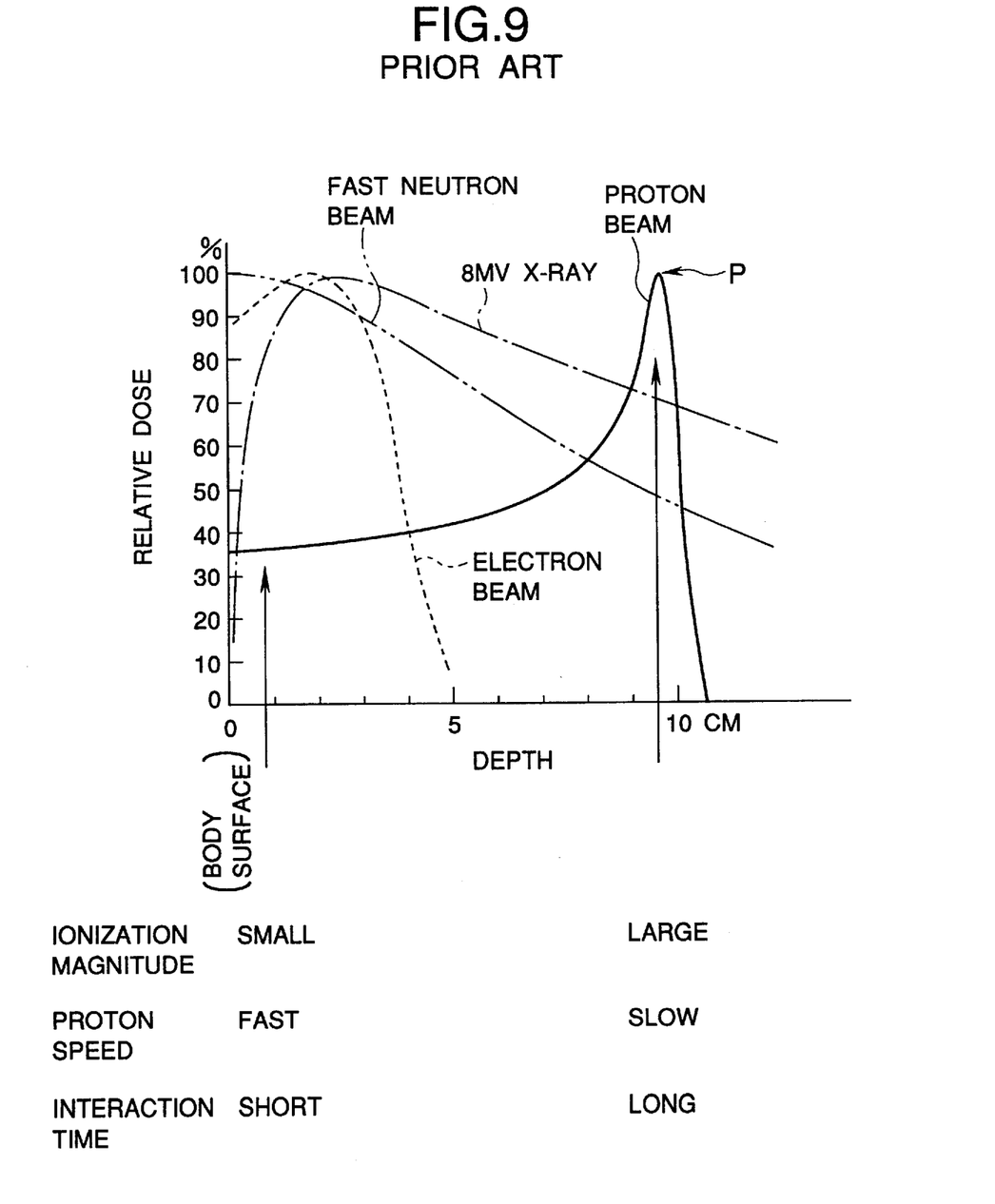
FIG. 9 gives graphs illustrating the principle underlying the proton radiation therapy.

Conventional cancer therapy based on radiation of active rays uses X-rays, gamma rays, electron beams, fast neutron beams, etc. These active rays, as shown in FIG. 9, become the strongest at sites close to the surface of a patient, and thus may inflict damages on normal tissues close to the body surface when those rays are directed towards a cancer in a deeper part of the body. By the way, a proton or a particle which comes into being when a hydrogen atom has been removed of the electron, has a positive charge, and has a mass 1836 times as large as that of electron, can be accelerated under a high energy state by an accelerator to give a proton beam. The proton beam is characterized by having the maximum dose peak or a Bragg peak P at a certain depth from the body surface, and then declining rapidly to zero.

This is because, as the electric force a proton exerts on electrons becomes large in proportion to its proximity to the latter, when the proton has a high kinetic energy and runs at a high speed, the time for the proton to interact with nearby electrons is short, and ionization is small in magnitude, but, when it loses the kinetic energy to nearly make a stop, the time for interaction becomes long and ionization rapidly increases in magnitude.

Thanks to this nature peculiar to protons, it is possible to apply proton beams for cancer therapy keeping normal cells other than a cancer comparatively free from damages, even if the cancer lies in a deeper part of the body. Further, as the radiation-based biological effect (RBE) of a proton beam is nearly equal to that of X-rays, the proton radiation therapy is advantageous in that it can make the most of knowledge and experience accumulated in the field of conventional X-ray radiation therapy. With these features, the proton radiation therapy device is being introduced as a therapy means to treat a cancer without removing any functional organs and encroaching on the quality of life.

In the radiation therapy of cancer, it is ideal to concentrate a lethal dose of active rays onto the cancer alone without inflicting any irreversible damages to nearby normal tissues. The Proton radiation therapy, as shown in FIG. 9, exploits the feature characteristic with protons that a proton beam incident on a substance gives the maximum dose or Bragg peak P just before it ceases to move. Namely the therapy in question aims at achieving this ideal by covering only the cancerous lesion with that Bragg peak.

By the way, protons obtained from an accelerator are in the form of a slender beam, and its energy is constant (the depth of Bragg peak is also constant). On the other hand, cancerous lesions are varied in size and have complex shapes, and their depths in the body are not constant. Further, the density of tissues through which a proton beam must pass is not constant neither. Accordingly, to achieve an effective radiation therapy, it is necessary to (1) enlarge the proton beam to have a sufficient width to cover the whole cancer lesion in one radiation; (2) adjust the beam energy according to the depth of lesion; (3) give a sufficient energy distribution in depth so that the whole cancer lesion having a certain depth can receive a uniform irradiation; and (4) make corrections according to the irregularities in contour of the lesion, and in density of the tissues through which the proton beam must pass.

It is also necessary to accurately focus the proton beam which has been adjusted in accordance with the shape and depth of a tumor, onto the cancerous lesion in the body of a patient following the radiation condition as determined previously, and to adjust radiation so that its dose and distribution occur as designed, and fall within tolerable errors.

To achieve above, it is necessary not only to reproduce the initially designed distribution of dose by properly adjusting the irradiation field forming unit including a bolus and a collimator, but also to accurately determine the radiation position of a proton beam with respect to the patient.

To attain this object, a rotating radiation chambers for radiation therapy has been developed which has a radiation beam irradiating section rotatable round the patient.

Figure 10:
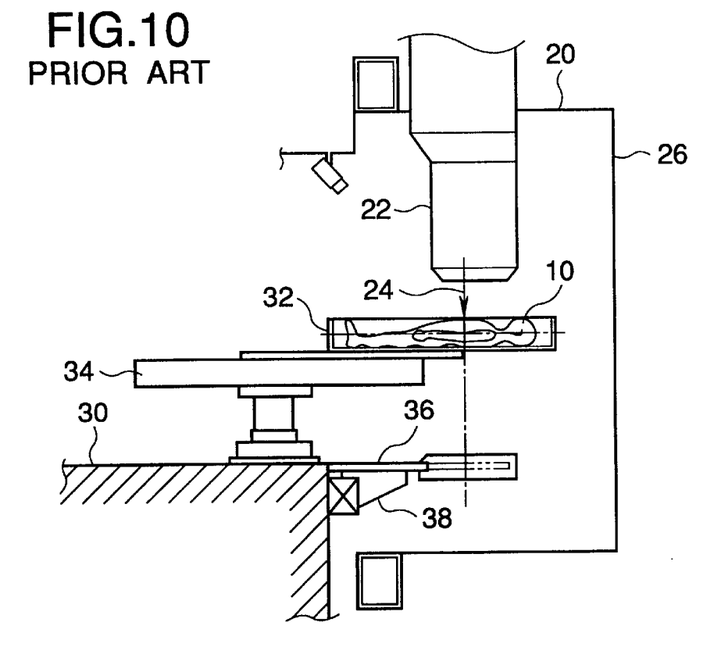
FIG. 10 gives a longitudinal sectional view illustrating how a conventional rotating radiation chamber having a projecting deck is constituted.
Figure 11:
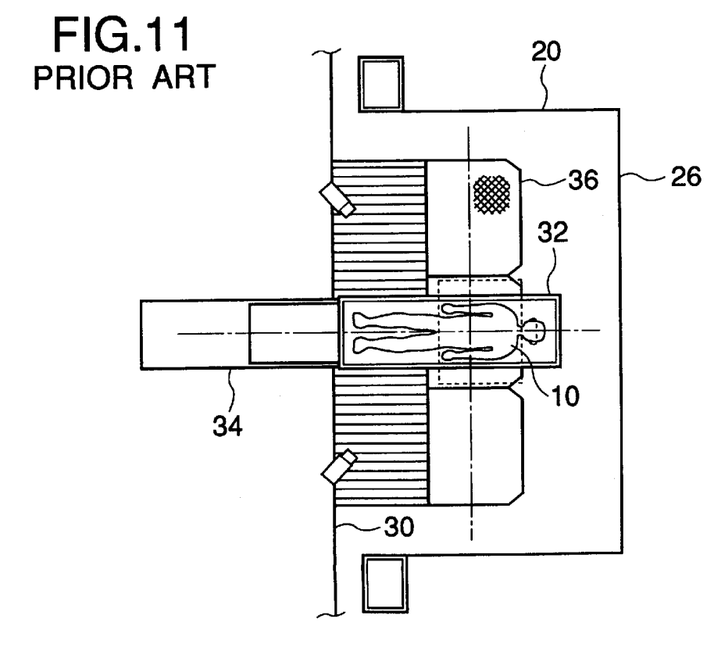
FIG. 11 gives a longitudinal sectional view of the chamber of FIG. 10, viewed from upward.
Figure 12:
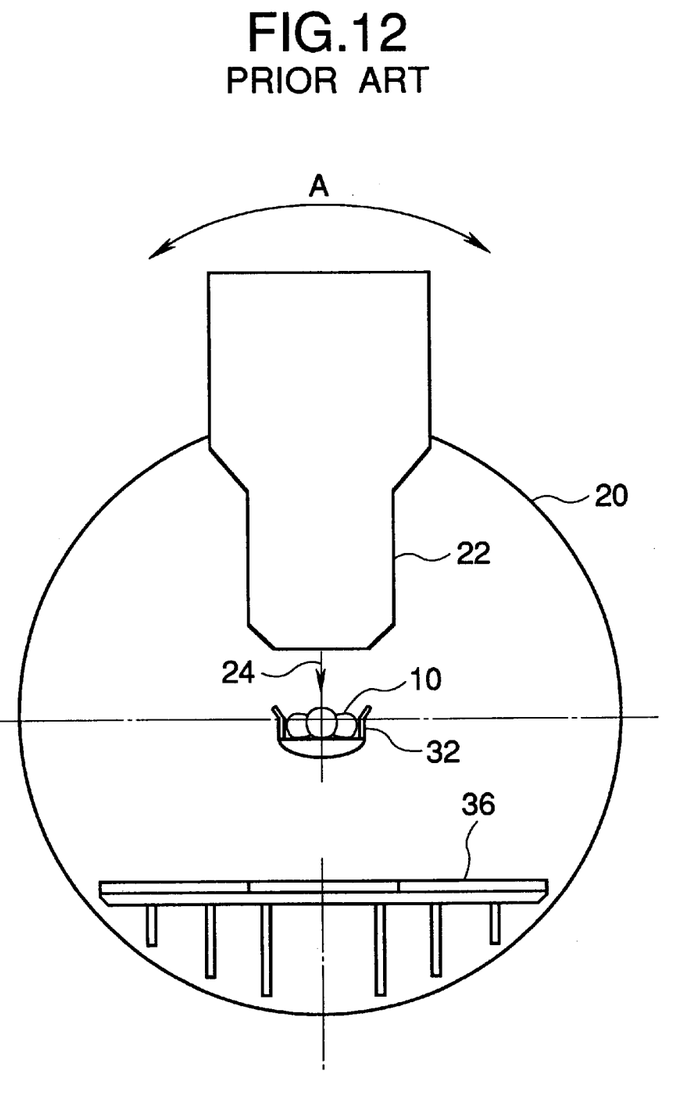
FIG. 12 gives a cross-sectional view of the chamber of FIG. 10.

However, as shown in FIGS. 10 to 12, the conventional rotating radiation chamber is so constructed as to push forward a projecting deck 36 as needed, in synchrony with a radiation beam irradiating section 22, together with a treatment bed 32 which is also driven forward from the housing base 30 by a bed driving mechanism 34, into a rotating capsule 20 which rotates round a patient 10 as indicated by the arrow of FIG. 12. Thus, when the radiation beam irradiating section 22 rotates until it comes beneath the treatment bed 32 to allow the radiation beam 24 to strike the patient 10 from a proper direction, the radiation beam irradiating section 22 and the projecting deck 36 interfere each other in their paths. Accordingly, a deck driving mechanism 38 and its control section must be added to project or retreat the projecting deck 36, in accordance with the position of radiation beam irradiating section 22. This complicates the structure. Further, as the deck driving mechanism 38 has to be installed on the housing base 30 on the same side with the rotating capsule 20, and on the same side the bed driving mechanism 34 is also installed, the deck driving mechanism 38 might interfere with the bed driving mechanism 34 but for some preventive means against it. Avoiding such interference with the bed driving mechanism 34 would further complicate the structure of deck driving mechanism 38. Furthermore, when the radiation beam irradiating section 22 comes downwards, and the projecting deck 36 is retreated, access to the interior of rotating capsule 20 becomes impossible. Still further, as the projecting deck 36 and the rotating capsule 20 are entities independent of each other, they have inevitably a space between them, through which a hard object may fall down, or their existence limits the work space. Still further, although a back panel 26 is installed against the background within the rotating capsule 20 to form a part of the enclosure surrounding the patient 10, but the floor is open. Therefore when the projecting deck 36 is retreated, the distance from the treatment bed 32 to the floor to be lengthened because then the inner surface of rotating capsule 20, instead of the projecting deck 36, forms the floor, which may cause a fear in the patient 10.

SUMMARY OF THE INVENTION

This invention is proposed to solve above problems inherent to the conventional device, and aims at providing a rotating radiation chamber for radiation therapy which allows a horizontal access floor to always cover the inner surface of rotating radiation chamber regardless of the rotating position of radiation beam irradiation section, and to always lie beneath the treatment bed.

This invention solves above problems by providing a rotating radiation chamber having a radiation beam irradiating section capable of rotating round a patient which comprises: fixing and moving ring rails sandwiching a moving route of the radiation beam irradiating section therebetween; a moving floor comprising a continuous series of multiple plates connected with each other freely flexible through links and placed within cylindrical passage with a semicircular cross-section having a horizontal floor and formed between the fixing and moving ring rails; and a driving means which moves the moving floor in synchrony with the rotation of the radiation beam irradiating section, and meanwhile rotates the moving ring rail in the reverse direction by the same distance.

Further, the chamber may have a safety means to inactivate the driving means when the difference in relative position between the fixing ring rail and the moving ring rail exceeds a predetermined limit.

According to this invention, even when the rotation gantry is put into rotation, a horizontal floor to act as an access floor to the treatment bed and radiation beam irradiating section is maintained horizontal. As this horizontal floor acts as an access floor continuous with the inner wall of gantry, it widens the work space. As it has no gaps, its design gives a good outlook. Furthermore, as the distance from the treatment bed to the moving floor is short and constant, the patient feels no fear. Still further, the driving mechanism is simple, and is placed within the gantry, the space in front of the gantry is available as a space for the treatment bed driving mechanism, and allows the treatment bed to enjoy a freer movement than is otherwise possible.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DESCRIPTION OF THE PREFERRED EMBODIMENTS

Preferred embodiments of the present invention will be explained hereunder.

Figure 1:
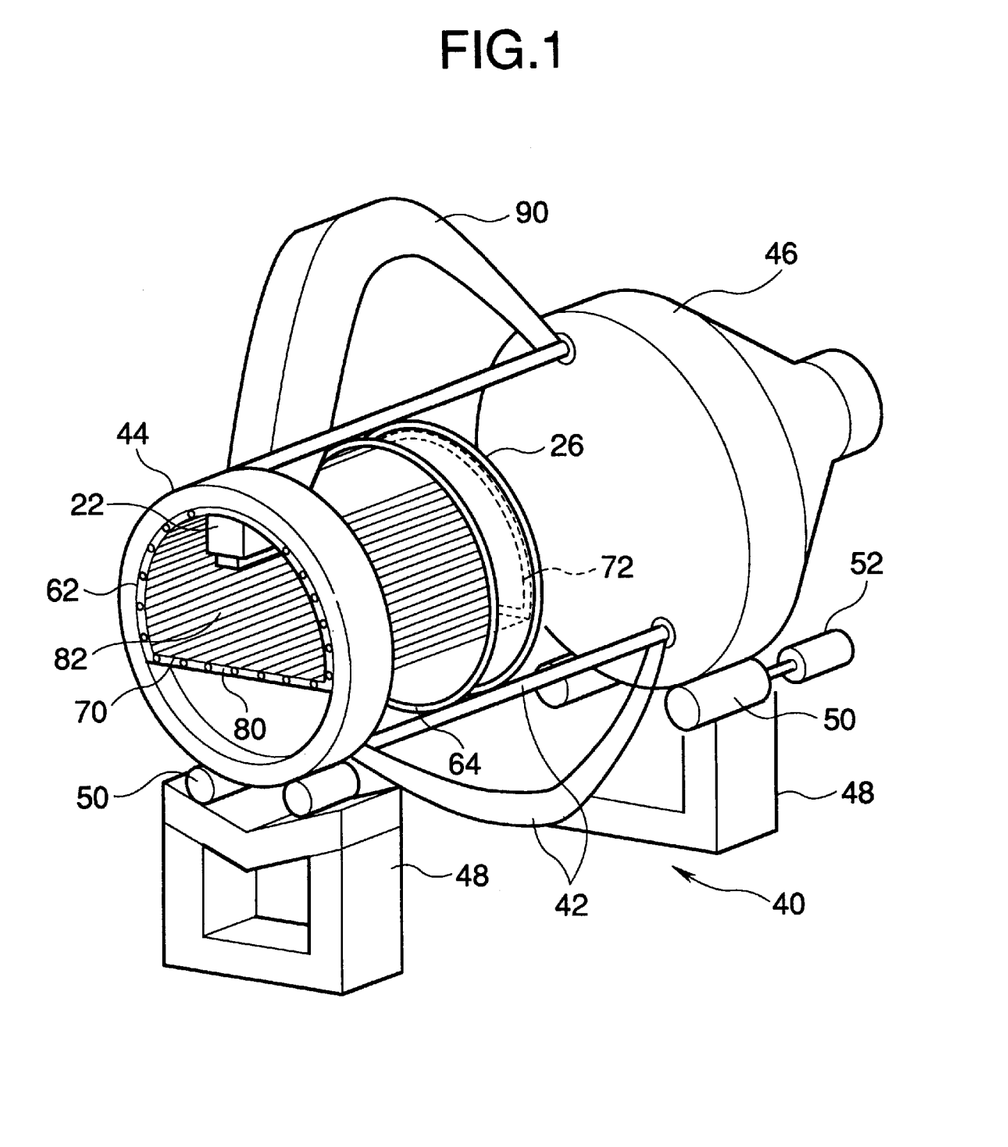
FIG. 1 gives a perspective view, viewed from an anterior, oblique angle, of the parts of interest of an embodiment of this invention.
Figure 2:
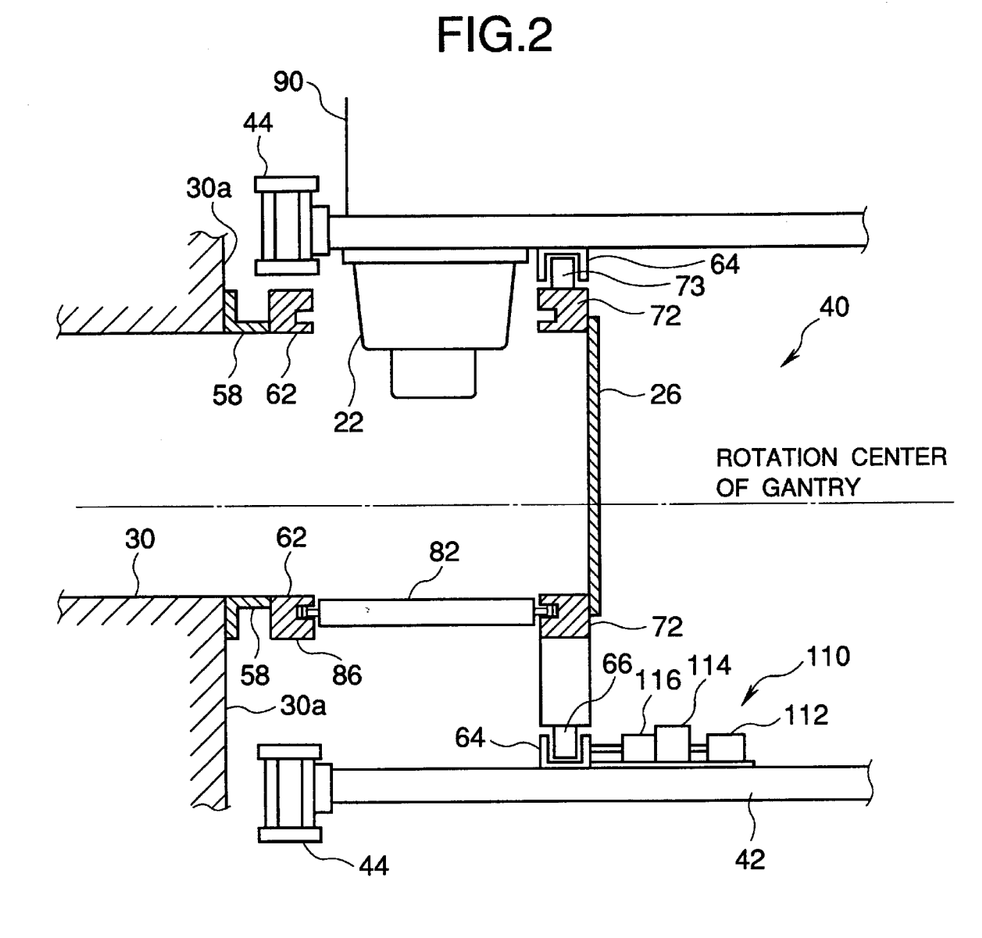
FIG. 2 gives a longitudinally cut sectional view illustrating the composition of a rotation gantry of the embodiment.
Figure 3:
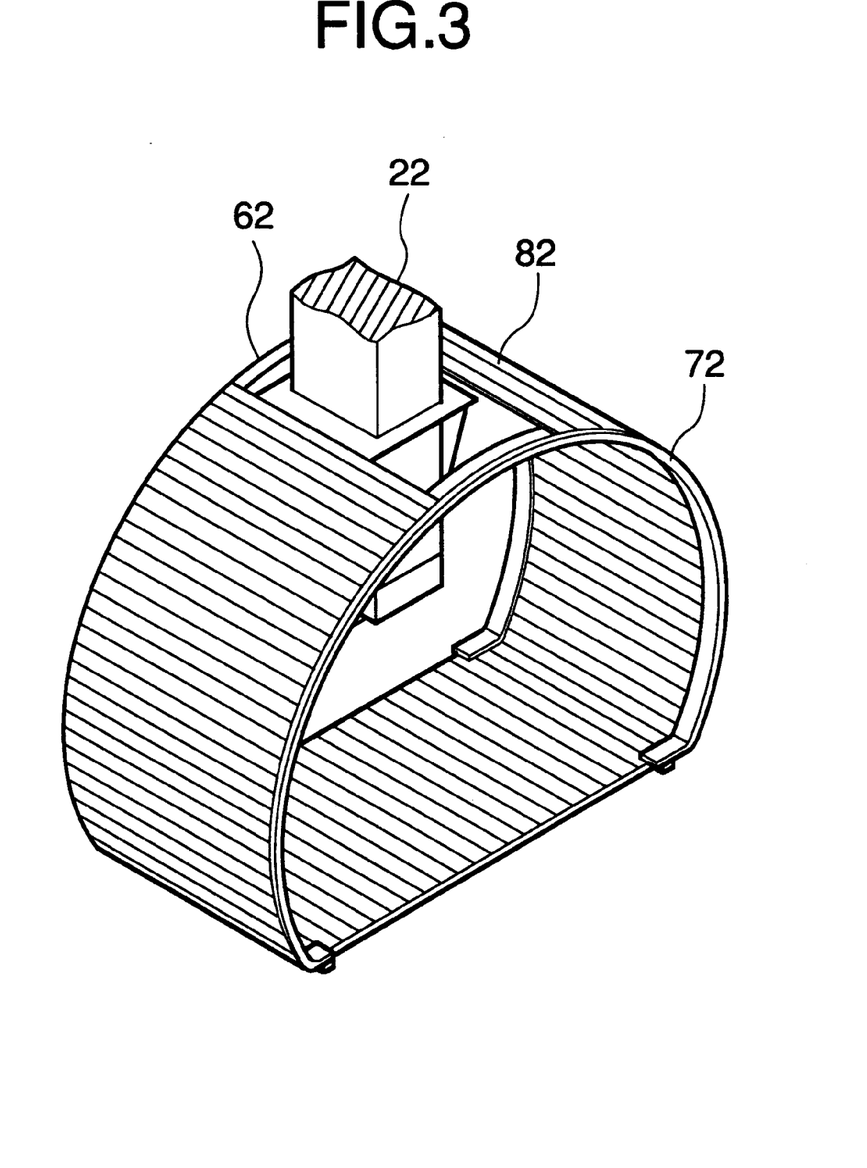
FIG. 3 gives a perspective view, viewed from a posterior, oblique angle, of the entire body of a moving floor of the embodiment.

As shown in FIGS. 1 to 3, the rotation gantry 40 according to this invention comprises: a fixing ring rail 62 which is held by a support 58 fixed to the housing wall 30a, and a moving ring rail 72 which can freely rotate in synchrony with the rotation of said radiation beam irradiating section 22, being held by a support ring 64 to which is fixed a rear surface panel 26 to form a part of the enclosure surrounding the patient, with four support rolls 66, for example, both ring rails are installed to sandwich the moving route of the radiation beam irradiating section 22; and a moving floor 82 which consists of a continuous series of multiple plates 84 connected freely flexible to each other through links, and is installed in a cylindrical passage 80 with a semicircular cross-section having a horizontal floor and formed between the fixing and moving ring rails 62 and 72; and a driving mechanism (described later) which moves the moving floor 82 in the passage 80 in synchrony with the rotation of the radiation beam irradiating section 22, and meanwhile rotates the moving ring rail 72 in the reverse direction by the same distance.

In FIGS. 1 and 2, 90 stands for a magnet support which not only supports a beam transport magnet forming the last element of a beam transporting device which ensures the stable trajectory of a proton beam generated by a proton accelerator (not illustrated here) including a cyclotron and energy selection system (ESS) for accelerating protons, modifying the energy of extracted proton beam, and limiting the dispersion of energy thereof, and therewith transports the beam to the rotation gantry 40 with only a small loss; but also acts as a space frame to fix the radiation beam irradiating section 22.

The rotation gantry 40 has a front ring 44 and a rear ring 46 connected by a space frame 42 which form together a rotating cylindrical body. The front ring 44 and rear ring 46 are placed on respective bases 48 with gantry support rolls 50 (eight in front side, eight in rear side, for example) inserted between the ring and respective base. Of these support rolls, for example, two support rolls on the rear base are driven by a gantry driving motor 52, thereby to put the gantry 40 into rotation.

Figure 4:
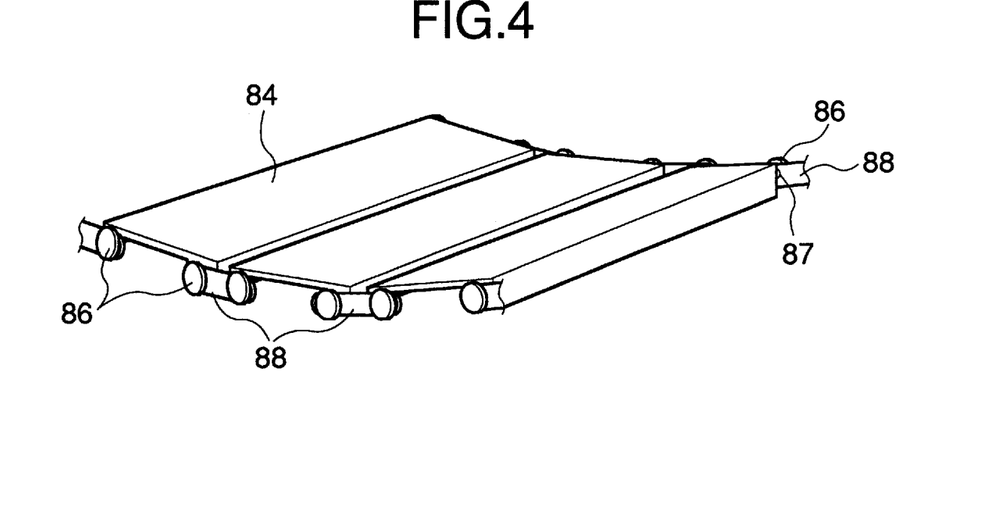
FIG. 4 gives a perspective view illustrating how the moving floor employed for the embodiment is constituted.

On both ends of each of plates 84 constituting the moving floor 82, as shown in detail in FIG. 4, are attached wheels 86 which run on the fixing ring rail 62 or on the moving ring rail 72, for example, two for front end and two for rear end. To the shaft 87 of paired wheels 86 are attached links 88 to join the adjacent plates 84.

Figure 5:
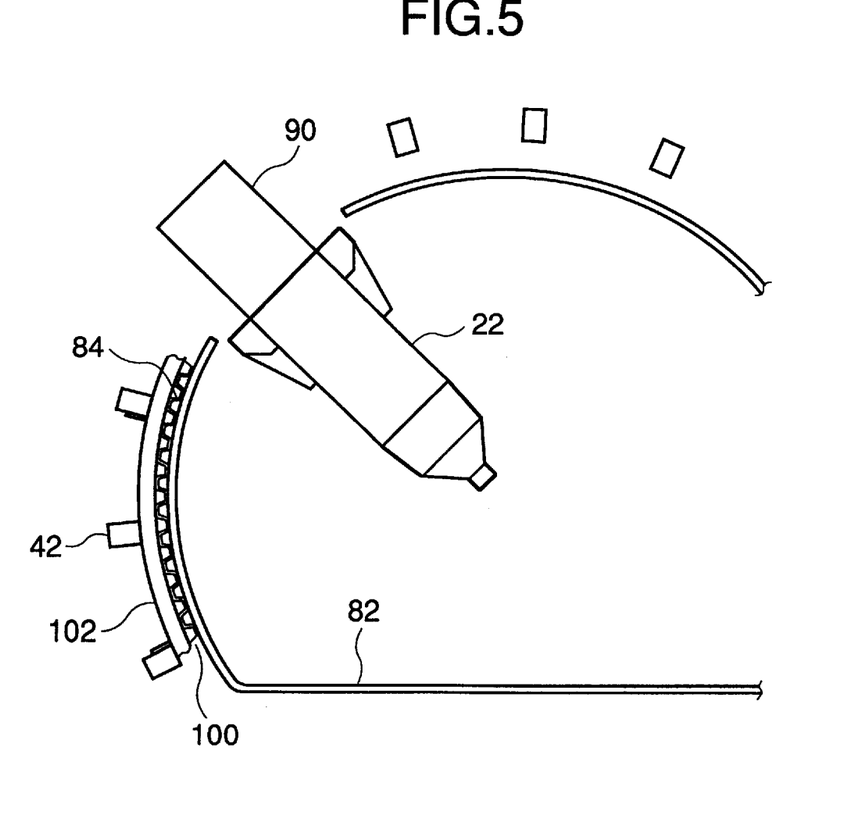
FIG. 5 gives a cross-sectional view illustrating how the enclosure of rotation gantry of the embodiment is constituted.

On the outer wall of the moving floor passage 80 formed by the fixing ring rail 62 and moving ring rail 72 fixed is, to hook the moving plates as shown in FIG. 5, a toothed latch 100 which is fixed to a latch support 102 which is, in turn, fixed to the space frame 42. Therefore, when the rotation gantry 40 is put into rotation, the moving floor 82 is pulled in association, and moves along the moving floor passage 80 formed by the fixing ring rail 62 and moving ring rail 72.

Figure 6:
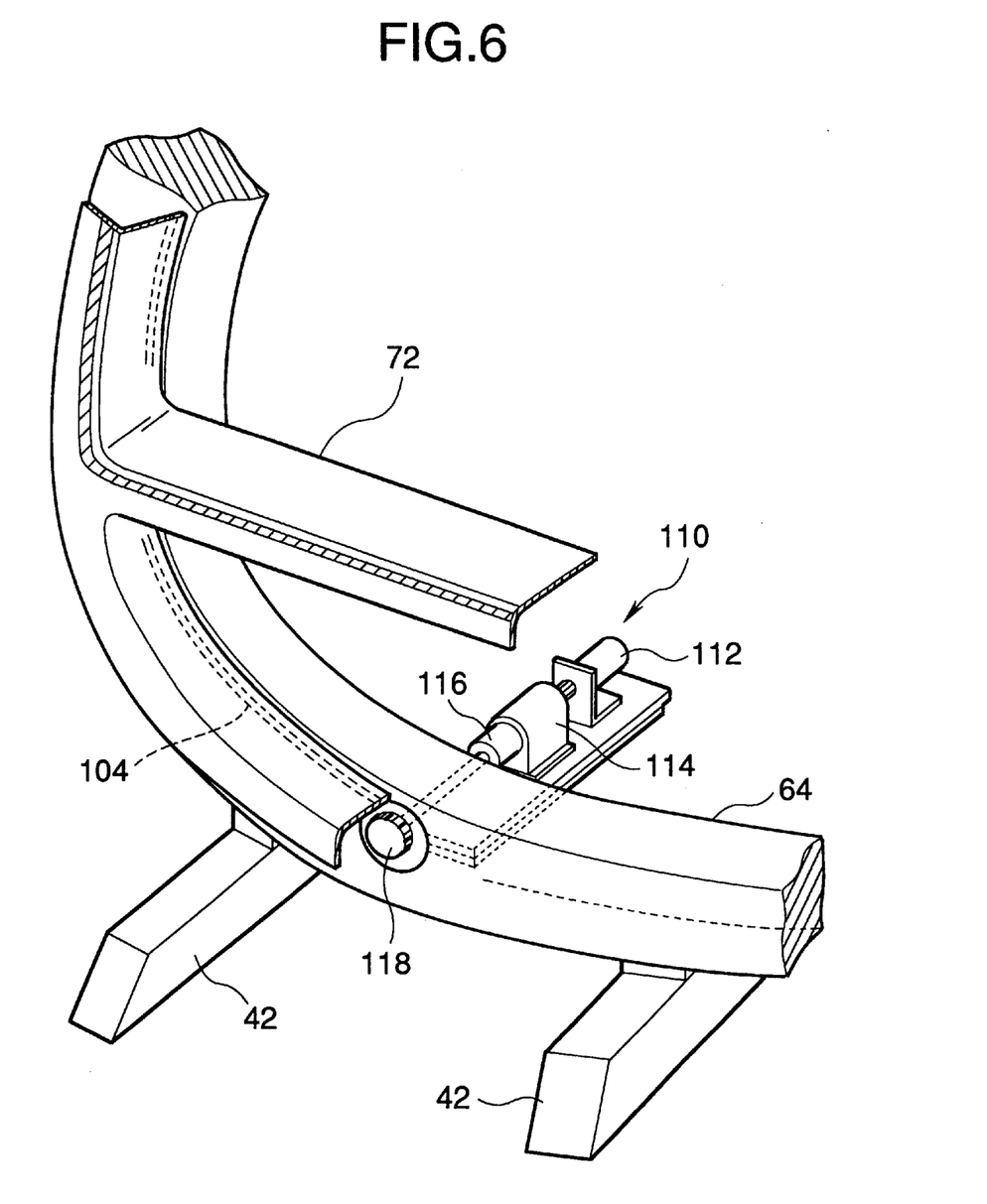
FIG. 6 gives a perspective view, viewed from front, illustrating how a ring rail driving mechanism employed for the embodiment is constituted.
Figure 7:
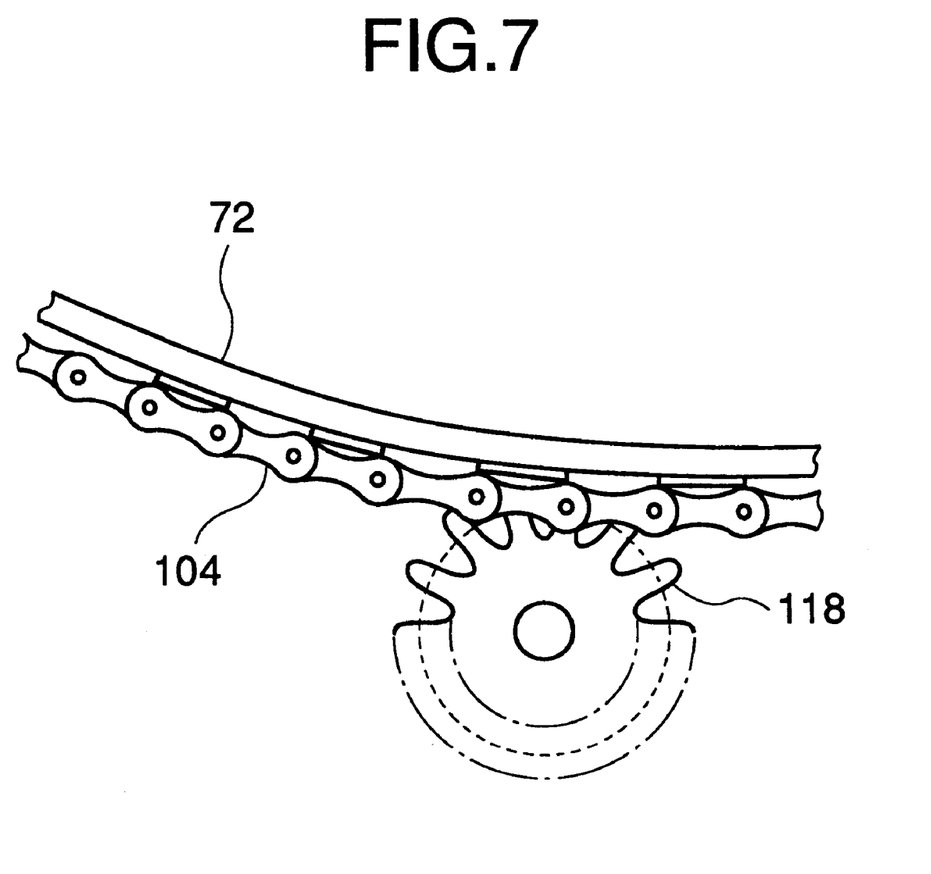
FIG. 7 gives a cross-sectional view illustrating how the conveyer chain of a moving ring rail and a sprocket engage with each other.

On the outer periphery of moving ring rail 72 is fitted a conveyor chain 104 as shown in FIGS. 6 and 7, which, being driven by a ring rail driving unit 110 including a ring rail driving motor 112 and a decelerator 114 fixed to a support ring 64, which is fixed to the inside of gantry frame 42, via a sprocket 111 which is rotated via a clutch 116 by the motor 112 and decelerator 114, moves in synchrony with the rotation of gantry 40, moving, however, in the reverse direction by the same distance. Accordingly, regardless of how much the rotation gantry 40 rotates, the absolute position of moving ring rail 72, or its relative position (phase angle) relative to the fixing ring rail 62 is kept constant, and thus the moving floor passage 80 is also kept at the same position.

Figure 8:
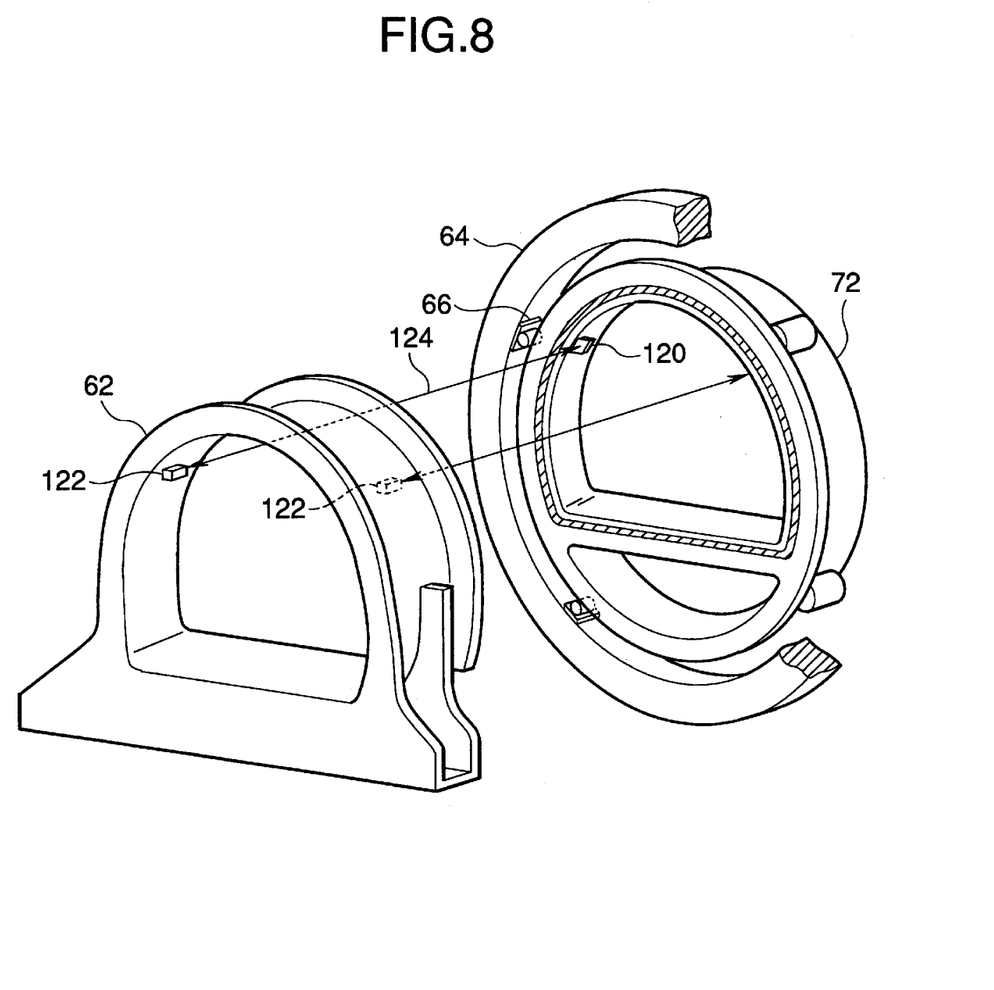
FIG. 8 gives a disintegrated, perspective view, viewed from an anterior, oblique angle, illustrating how a laser tilt sensor and a reflecting plate are installed in the embodiment.

Further, in this embodiment, two reflecting plates 120 are attached on the inside of moving ring rail 72 as shown in FIG. 8, which reflect laser beams 124 emanating from laser-based tilt sensors 122 attached to the fixed ring rail 62, so that one can judge, by checking the reflection of laser beams from the sensors, whether the displacement of moving ring rail 72 relative to the fixed ring rail 62 exceeds a predetermined limit or not. If the displacement of moving ring rail 72 relative to the fixed ring rail 62 is so large that a laser beam reflected from one reflecting plate 120 passes out of the range of the corresponding laser-based tilt sensor 122, the clutch 116 is disconnected to abolish the driving action of the ring rail driving mechanism 110, thereby to prevent the moving floor 82 from being broken due to a twist between the front and rear rails. For above operation, two sets of laser-based tilt sensor 122 and reflecting plate 120 are implemented. This is because, even if the beam path of one set is blocked by the radiation beam irradiating section 22 which is rotating, one can check the relative position in question by resorting to the other.

The back panel 26 and the moving floor 82 covering almost the entire surface except for the region close to the radiation beam irradiating section 22 of rotation gantry 40 constitute the enclosure, and thus prevent the patient and operator from seeing the iron frame structure of gantry and the outside. Hence, the patient and operator are shield from visual and auditory stimuli, and highly safe and given a comfort.

With this embodiment, when the gantry 40 is put into rotation, the moving ring rail 72 rotates in synchrony therewith in the reverse direction, and, while keeping the bottom floor horizontal, in cooperation with the opposite fixed ring rail 62, maintains the passage of the moving floor 82 constant. In addition, the radiation beam irradiating section 22 and the latch 100 to drive the moving floor 82 are also put into rotation, and, as a consequence, the moving floor 82, without interfering with the movement of radiation beam irradiating section 22, moves the space between the two ring rails 62 and 72, maintaining constant the horizontally kept access floor on which the operator can stand to make maintenance works on the radiation beam irradiating section 22 or to adjust the position of patient 10 on the bed 32.

The fixed ring rail 62 has, on its inner surface, laser type tilt sensors 122 through which the movement of moving ring rail 72 is always monitored, and, as soon as the displacement of moving ring rail 72 exceeds a predetermined limit, the clutch 116 of ring rail driving mechanism 110 is disconnected, to arrest the rotation of gantry. The moving ring rail 72 has its center of gravity shifted downward on account of its structure, and thus, when the clutch 116 is discontinued, it returns to its original position by its own weight, so that the bottom surface is kept horizontal.

This embodiment is provided with a safety means comprising two sets of laser type tilt sensor 122 and reflecting plate 120, and thus highly safe. In addition, the former that requires a wiring and complicated structure, is attached on the fixed ring rail 62 while the latter to the moving ring rail 72, and thus installment and maintenance thereof are easy. The safety means, however, is not limited to above. One set will give the same result as long as the light path remains undisturbed, or it is possible to detect the relative displacement between the moving ring rail 72 and fixed ring rail 62 by other means than above. Or, it is possible to introduce a safety means which consists of detecting some other parameter than the displacement of moving ring rail here concerned.

In this embodiment, this invention is explained with an exclusive reference to a proton radiation therapy system, but this invention should not be limited to this. Apparently, the present invention can be applied with the same profit to the radiation therapy systems based on the use of X-rays, electron beams and so on.

What is claimed is:

1. A rotating radiation chamber for radiation therapy which has radiation beam irradiating section rotatable around a patient comprising:

fixed and moving ring rails sandwiching a moving route of the radiation beam irradiating section therebetween;

a moving floor comprising a continuous series of multiple plates connected with each other freely flexible through links and placed within a cylindrical passage with a semicircular cross-section having a horizontal floor and formed between the fixed and moving ring rails, and a driving means which moves the moving floor in synchrony with the rotation of radiation beam irradiation section, and meanwhile rotates the moving ring rail in reverse direction by same distance.

2. The rotating radiation chamber as set forth in claim 1 which is further provided with a safety means which abolishes operation of the driving means, if relative displacement between the fixed ring rail and the moving ring rail exceeds a predetermined limit.

3. The rotating radiation chamber as set forth in claim 1 wherein the fixed ring rail is supported by a support fixed to a wall of an outer housing, and the moving ring rail is supported by a support ring by way of plural support rolls.

4. The rotating radiation chamber as set forth in claim 3 wherein a rear surface panel to form a part of enclosure surrounding the patient is fixed to the support ring.

5. The rotating radiation chamber as set forth in claim 1 wherein the moving floor has plural wheels placed on both sides of the plates and running either on the fixed ring rail or on the moving ring rail, and links fitted to shaft of paired wheels to join adjacent plates together.

6. The rotating radiation chamber as set forth in claim 1 wherein the driving means comprises:

a toothed latch which is fixed to a latch support stabilized on space frame of the radiation beam irradiation section, to pull the moving floor by hooking the moving floor, in synchrony with the rotation of radiation beam irradiation section; and a ring rail driving mechanism which rotates, by spinning a sprocket to engage with a conveyor chain fixed on outer periphery of the moving ring rail, the moving ring rail in synchrony with the rotation of radiation beam irradiating section by same distance in reverse direction.

7. The rotating radiation chamber as set forth in claim 2 wherein the safety means comprises a laser type tilt sensor attached to either the fixed ring rail or the moving ring rail, and a reflecting plate attached to the other ring rail.

8. The rotating radiation chamber as set forth in claim 7 which has plural sets of the laser type tilt sensor and the reflecting plate.

9. The rotating radiation chamber as set forth in claim 6 which has a clutch to abolish operation of the ring rail driving mechanism, when a relative displacement between the fixed ring rail and moving ring rail exceeds a predetermined limit.

10. The rotating radiation chamber as set forth in claim 9 wherein, as center of gravity of the moving ring rail is shifted downward, the moving ring rail returns by its own weight to the original position to keep bottom surface horizontal, when the clutch is disconnected.

* * * * *